(12) United States Patent
Saracen et al.

(10) Patent No.: US 8,457,279 B2
(45) Date of Patent: *Jun. 4, 2013

(54) PATIENT POSITIONING ASSEMBLY

(75) Inventors: Michael Saracen, Oakland, CA (US);
James Wang, Palo Alto, CA (US); Euan Thomson, Los Gatos, CA (US); Eric Earnst, Saratoga, CA (US); Chris Raanes, Portola Valley, CA (US); Mohan Bodduluri, Palo Alto, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/793,453

(22) Filed: Jun. 3, 2010

(65) Prior Publication Data

US 2010/0275927 A1    Nov. 4, 2010

Related U.S. Application Data

(63) Continuation of application No. 10/881,315, filed on Jun. 30, 2004, now Pat. No. 7,860,550.

(60) Provisional application No. 60/560,318, filed on Apr. 6, 2004.

(51) Int. Cl.
*G21K 5/10*    (2006.01)

(52) U.S. Cl.
USPC .................. 378/69; 378/35; 378/68; 378/427

(58) Field of Classification Search
USPC ......... 378/65, 197, 209; 600/407, 424; 601/5; 606/424; 74/490.01–490.05; 219/124.35, 219/639; 221/210; 318/560
See application file for complete search history.

(56) References Cited

U.S. PATENT DOCUMENTS

| | | | |
|---|---|---|---|
| 2,295,006 A | 9/1942 | Philips | |
| 2,787,506 A | 4/1957 | Travisano | |
| 3,069,543 A | 12/1962 | Sazavsky | |
| 3,082,322 A * | 3/1963 | Koerner et al. | ........... 378/65 |
| 3,262,133 A | 7/1966 | Beitzel | |
| 3,640,520 A | 2/1972 | Wieland et al. | |
| 3,806,109 A | 4/1974 | Weber et al. | |
| 3,997,926 A | 12/1976 | England | |
| 4,259,756 A | 4/1981 | Pace | |
| 4,579,323 A | 4/1986 | Brendl et al. | |
| 4,603,845 A | 8/1986 | Schmedemann | |
| 4,618,133 A | 10/1986 | Siczek | |
| 4,672,697 A | 6/1987 | Schurch | |
| 4,697,802 A | 10/1987 | Brendl et al. | |
| 4,749,177 A | 6/1988 | Schafer et al. | |

(Continued)

FOREIGN PATENT DOCUMENTS

| | | |
|---|---|---|
| EP | 1121957 | 8/2001 |
| JP | 1-214373 | 8/1989 |

(Continued)

OTHER PUBLICATIONS

Response to Rule 312 Communication for U.S. Appl. No. 10/881,315 mailed Jun. 2, 2010, 2 pages.

(Continued)

*Primary Examiner* — Elmer Chao
(74) *Attorney, Agent, or Firm* — Lowenstein Sander LLP

(57) ABSTRACT

A patient positioning assembly is described. The patient positioning assembly including a plate member rotatably mounted on a base member, and an arm extending between a first end and a second end, wherein the first end is rotatably attached to the plate member. The patient positioning assembly further including a support device rotatably attached to the second end of the arm to support a patient thereon, with the support device is configured to move the patient in at least five degrees of freedom.

10 Claims, 11 Drawing Sheets

U.S. PATENT DOCUMENTS

| | | | |
|---|---|---|---|
| 4,841,585 A | 6/1989 | Masuzawa | |
| 4,872,657 A | 10/1989 | Lussi | |
| 5,022,810 A | 6/1991 | Sherrow et al. | |
| 5,044,354 A | 9/1991 | Goldhorn et al. | |
| 5,207,223 A | 5/1993 | Adler | |
| 5,299,334 A | 4/1994 | Gonzalez | |
| 5,345,632 A | 9/1994 | Langenaeken et al. | |
| 5,361,436 A | 11/1994 | Hahn | |
| 5,386,453 A | 1/1995 | Harrawood et al. | |
| 5,427,097 A | 6/1995 | Depp | |
| 5,499,415 A | 3/1996 | McKenna | |
| 5,572,569 A | 11/1996 | Benoit et al. | |
| 5,613,254 A | 3/1997 | Clayman et al. | |
| 5,619,763 A | 4/1997 | Randolph et al. | |
| 5,655,238 A | 8/1997 | Stickley et al. | |
| 5,744,728 A | 4/1998 | Suita et al. | |
| 5,790,996 A | 8/1998 | Harfstrom | |
| 5,820,553 A | 10/1998 | Hughes | |
| 5,825,843 A | 10/1998 | Kobayashi | |
| 5,983,424 A | 11/1999 | Naslund | |
| 6,094,760 A | 8/2000 | Nonaka et al. | |
| 6,125,164 A | 9/2000 | Murphy et al. | |
| 6,138,302 A | 10/2000 | Sashin et al. | |
| 6,217,214 B1 | 4/2001 | Cabral et al. | |
| 6,222,544 B1 | 4/2001 | Tarr et al. | |
| 6,279,579 B1 | 8/2001 | Riaziat et al. | |
| 6,385,286 B1 | 5/2002 | Fitchard et al. | |
| 6,416,219 B1 | 7/2002 | Pflaum et al. | |
| 6,484,332 B2 | 11/2002 | Korver, II et al. | |
| 6,501,981 B1 | 12/2002 | Schweikard et al. | |
| 6,502,261 B1 * | 1/2003 | Harwood | 5/611 |
| 6,516,046 B1 | 2/2003 | Frohlich et al. | |
| 6,524,246 B1 | 2/2003 | Kelly et al. | |
| 6,617,852 B1 | 9/2003 | Danby et al. | |
| 6,651,279 B1 | 11/2003 | Muthuvelan | |
| 6,810,108 B2 | 10/2004 | Clark et al. | |
| 6,826,254 B2 * | 11/2004 | Mihara et al. | 378/64 |
| 6,865,253 B2 | 3/2005 | Blumhofer et al. | |
| 6,889,695 B2 | 5/2005 | Pankratov et al. | |
| 7,046,765 B2 | 5/2006 | Wong et al. | |
| 7,154,991 B2 | 12/2006 | Earnst et al. | |
| 7,166,852 B2 | 1/2007 | Saracen et al. | |
| 7,173,265 B2 | 2/2007 | Miller et al. | |
| 7,298,385 B2 | 11/2007 | Kazi et al. | |
| 2002/0072813 A1 | 6/2002 | Ito | |
| 2002/0077545 A1 | 6/2002 | Takahashi et al. | |
| 2002/0188194 A1 | 12/2002 | Cosman | |
| 2002/0193685 A1 * | 12/2002 | Mate et al. | 600/424 |
| 2003/0048875 A1 | 3/2003 | Mihara et al. | |
| 2004/0172756 A1 | 9/2004 | Somasundaram | |
| 2005/0027285 A1 | 2/2005 | Ritter et al. | |
| 2005/0085710 A1 | 4/2005 | Earnst et al. | |
| 2005/0226377 A1 | 10/2005 | Wong et al. | |
| 2005/0228255 A1 | 10/2005 | Saracen et al. | |
| 2005/0234327 A1 | 10/2005 | Saracen et al. | |
| 2006/0002511 A1 | 1/2006 | Miller et al. | |
| 2006/0245543 A1 | 11/2006 | Earnst et al. | |

FOREIGN PATENT DOCUMENTS

| | | |
|---|---|---|
| JP | 4348895 A | 12/1992 |
| JP | 5111542 | 5/1993 |
| JP | 6182653 A | 7/1994 |
| JP | H11509461 A | 8/1999 |
| JP | 11313900 A | 11/1999 |
| JP | 2001-238923 | 9/2001 |
| JP | 2002191708 A | 7/2002 |
| JP | 2003-135539 | 5/2003 |
| JP | 2003-210594 | 7/2003 |
| JP | 2004166975 A | 6/2004 |
| KR | 2002-253687 | 9/2002 |
| WO | WO9413205 | 6/1994 |
| WO | WO9927839 | 6/1999 |
| WO | 0245642 A2 | 6/2002 |
| WO | 2005018735 A2 | 3/2005 |
| WO | WO-2005/018734 | 3/2005 |
| WO | 2005039472 A2 | 5/2005 |

OTHER PUBLICATIONS

Notice of Allowance for U.S. Appl. No. 10/881,315 mailed Apr. 1, 2010, 23 pages.
Office Action for U.S. Appl. No. 10/881,315 mailed Jun. 10, 2009, 24 pages.
Final Office Action for U.S. Appl. No. 10/881,315 mailed Jan. 16, 2009, 18 pages.
Office Action for U.S. Appl. No. 10/881,315 mailed Aug. 29, 2008, 21 pages.
Advisory Action for U.S. Appl. No. 10/881,315 mailed Jul. 17, 2008, 3 pages.
Final Office Action for U.S. Appl. No. 10/881,315 mailed Feb. 6, 2008, 21 pages.
Office Action for U.S. Appl. No. 10/881,315 mailed Feb. 23, 2007, 28 pages.
First Notice of Preliminary Rejection, Korean Patent Application No. 2006-7023241, issued Nov. 3, 2010, 7 pages, English translation.
First Notice of Preliminary Rejection, Korean Patent Application No. 2006-7023241, issued Nov. 3, 2010, 7 pages (non-English).
Japanese Office Action mailed Nov. 9, 2011, for Japanese Patent Application No. 2009-073432, 2 pages.
Supplemental Search Exam mailed Mar. 7, 2012, for EP Application No. 05733736.2, 6 pages.
Katuin, J.E. et al. (2002). "The Use of Industrial Robot Arms for High Precision Patient Positioning," Application of Accelerators in Research and Industry, 4 pages.
De Kock et al., Integrating an Industrial Robot and Multi-Camera Computer Vision Systems Into a Patient Positioning System for High-Precision Radiotherapy IThemba LABS, PO Box 722, Somerset West, 7129, South Africa, Mar. 24, 2004.
Fourth Office Action for Chinese Patent Application No. 200580018430.5, Date of Issue: Dec. 25, 2009, 28 pages.
Alejandro Mazal et al., "Robots in patient positioning for external radiotherapy", presentation, 46th American Association of Physicists in Medicine Annual Meeting, Pittsburgh, Jul. 2004.
"Adept Technology Announces Extension of SmartServo Architecture to SCARA Robots", Adept Technology, Inc., News Article, Sep. 18, 2002, 2 pages.
"Adept Technology Introduces Four New SCARA Robots with Adept's SmartServo Architecture", Adept Technology, Inc.—News Article, Apr. 14, 2003, 2 pages.
"EC Series SCARA Robots", Seiko EC SCARA Robots, 2003, Epson America, Inc., 3 pages, downloaded Nov. 18, 2004, http://www.seikorobots.com/products/ecrbts.htm.
"EH Series SCARA Robots", Epson EH SCARA Robots, 2 pages, downloaded Nov. 18, 2004, http://www.robots.epson.com/products/ehrbts.htm.
"SCARA Robot—Adept Cobra s600", SCARA Robot—Adept Cobra s600—tabletop factory automation, 2 pages, downloaded Nov. 18, 2004, http://www.adept.com/main/products/robots/cobra_s600.shtml, 2 pages.
Adept Cobra s600 Robot with CS or CX (90565-00x), Adept Technology, Inc., Nov. 5, 2004, 5 pages.
"Adept SmartCartesian™", Adept Technology, Inc., Mar. 26, 2002, 1 page.
"HS & HM Series SCARA Robots", Motoman, Solutions in Motion, 4 pages, 2002 Motoman, Inc. Sep. 2002.
"EPH4000" Motoman, Solutions in Motion, 2 pages, 2004 Motoman, Inc., Feb. 2004.
"AdeptXL SCARA Robots", downloaded Nov. 30, 2004, http://www.adeot.com/main/products/robots/AdeptXL.shtml, 1 page.
"AdeptThree XL SCARA Robot", 2000-2004, Adept Technology, Inc., downloaded Nov. 30, 2004, http://www.adept.com/main/products/robots/AdeptThree.shtml, 1 page.
Pro Six (6-Axis), Epson Pro Six 6-Axis Robots (also called Vertical Articulated robots), 3 pages, downloaded Nov. 30, 2004, http://www.robots.epson.com/products/prosixrbts.htm.
"E2H SCARA Robots", Epson E2H SCARA Robots, downloaded Nov. 30, 2004, http://www.robots.epson.com/products/e2hrbts.htm, 3 pages.
"UP6" Payload: 6 kg, Motoman, Solutions in Motion, 2 pages., 2003 Motoman Inc., Oct. 2003.

"UP20MN" Payload: 20 kg, Motoman, Solutions in Motion, 2 pages, 2004 Motoman Inc., Mar. 2004.
"HP20" Payload: 20 kg, Motoman, Solutions in Motion, 2 pages, 2004 Motoman Inc., Apr. 2004.
"Motoman-CR50", Type: YR-CR50-A00, 1 page, http://www.motoman.com/products/robots/default.htm, 2001-2005, Motoman Inc., downloaded May 12, 2005.
"Welding One Step Ahead, Linear Units", Kuka Robot Group, downloaded Apr. 20, 2005, http://www.kuka.com/en/products/addons/linearunits/start.htm, 1 page.
"KR6", Kuka Robot Group, downloaded Nov. 17, 2004, http://www.kuka.com/en/products/robots/low/kr6/start.htm, 1 page.
"KR16", Kuka Robot Group, downloaded Nov. 17, 2004, http://www.kuka.com/en/products/robots/low/kr16/start.htm, 1 page.
"KR 16 KS" Kuka Robot Group, downloaded Nov. 17, 2004, http://www.kuka.com/en/products/robots/low/kr16__ks/start.htm, 1 page.
"KR 16 L6", Kuka Robot Group, downloaded Nov. 17, 2004, http://www.kuka.com/en/products/robots/low/kr16__16/start.htm, 1 page.
"KR 30-3", Kuka Robot Group, downloaded Nov. 17, 2004, http://www.kuka.com/en/products/robots/medium/kr30__3/start.htm, 1 page.
KR 30-3 KS, Kuka Robot Group, downloaded Nov. 17, 2004, http://www.kuka.com/en/products/robots/medium/kr30__3__ks/start.htm, 1 page.
KR 30 HA (High Accuracy), Kuka Robot Group, downloaded Nov. 17, 2004, http://www.kuka.com/en/products/robots/medium/kr30__ha/start.htm, 1 page.
"KR 60-3", Kuka Robot Group, downloaded Nov. 17, 2004, http://www.kuka.com/en/products/robots/medium/kr60__3/start.htm, 1 page.
"KR 60-3 KS", Kuka Robot Group, downloaded Nov. 17, 2004, http://www.kuka.com/en/products/robots/medium/kr60__3__ks/start.htm, 1 page.
KR 100 P (Series 2000), Kuka Robot Group, downloaded Nov. 17, 2004, http://www.kuka.com/en/products/robots/high/kr100__p__2000/start.htm, 1 page.
KR 150 K (Series 2000), Kuka Robot Group, downloaded Nov. 17, 2004, http://www.kuka.com/en/products/robots/high/kr150__k__2000/start.htm, 1 page.
"KR 500 570 PA/1", Kuka Robot Group, downloaded Nov. 17, 2004, http://www.kuka.com/en/products/robots/heavy/kr500__570__pa/start.htm, 1 page.
"Linear Units", Kuka Robot Group, downloaded Nov. 30, 2004, http://www.kuka.com/cgi-bin/MsmGo.exe?grab__id=11&page__id=9375232&query=Linear+Units&hiword=LINEAREN+LINEARLY+ Linear+UNIT+UNITE+UNITED+Units+, 1 page.
"KR 500 570 PA/1", Kuka Robot Group, downloaded Nov. 30, 2004, http://www.kuka.com/en/products/robots/heavy/kr500__570__pa/start.htm, 1 page.
"iThemba Labs Medical Radiation Group, New Treatment Station, Non-Orthogonal Beam Lines for Proton Therapy", Seite 1 von 2, downloaded Aug. 3, 2004, http://www.medrad.nac.ac.za/npther.htm, 12 pages.
KR 210-2 (Series 2000), Kuka Robots USA, downloaded Jan. 21, 2005, http://www.kuka.com/usa/en/products/robots/high/kr210__2__2000/start.htm, 1 page.
KR360/1, KR360 450 PA/1, KR 360 L150 P/1, KR 500/1, KR 500 570 PA/1, Mar. 1, 2005, cover sheet and pp. 13-22, 33-58.
"CyberKnife", Stereotactic Radiosurgery System using image-guided robotics, downloaded Nov. 16, 2004, http://www.accuray.com/ck/deliv18.htm, 3 pages.
Linac Scalpel, "RadioCameras™ System, Frameless Stereotactic Radiotherapy and Radiosurgery," Zmed Inc., 2001.
TomoTherapy Incorporated, "The Tomo® Advantage: TomoImage™", 2003.
TomoTherapy Incorporated, "A True Integrated Treatment System", 2003.
BrainLAB Radiotherapy Solutions, "A good idea perfected, ExacTRAC$^{xray6D}$, BrainLAB's unique X-Ray based targeting technology. Available as an upgrade to your existing Linac", 2003 BrainLAB AG.
Neurosurgery News, New Products/Press Releases, "Elekta Receives FDA Clearance for Elekta Synergy™, New radiotherapy system from Elekta combines x-ray volume imaging and treatment in a single platform", Fall 2003, pp. 17-18.
North American Scientific, NOMOS Radiation Oncology Division, "IMRT/IMRS Delivery System", 2003.
Varian Medical Systems, Oncology Systems, Treatment Delivery, Exact Couch™ Couch and Indexed Immobilization™, 1999-2005 Varian Medical Systems, Inc.
Milton K. Woo, Bryan Kim, "An investigation of the reproducibility and usefulness of automatic couch motion in complex radiation therapy techniques", Journal of Applied Clinical Medical Physics, vol. 3, No. 1, Winter 2002, pp. 46-50.
E.A. de Kock et al., "Integrating an Industrial Robot and Multi-camera Computer Vision Systems into a Patient Positioning System for High-precision Radiotherapy", Wednesday, Mar. 24, 2004, 6 pages, ISR 2004 Symposium, Mar. 23-26, 2004.
European Search Report, 04782483.4-2305, PCT/US2004/028011 dated Oct. 16, 2007, 5 pages.
"International Search Report", International Searching Authority, PCT/US2004/28011, Oct. 31, 2005, 3 pages.
"Written Opinion of the International Searching Authority", International Searching Authority, PCT/US2004/28011, Oct. 31, 2005, 5 pages.
"PCT International Preliminary Report on Patentability", PCT/US2004/28011, Mar. 15, 2006, 5 pages.
"International Search Report", International Searching Authority, PCT/US2006/18017, Jan. 11, 2007, 4 pages.
"Written Opinion of the International Searching Authority", International Searching Authority, PCT/US2006/18017, Jan. 11, 2007, 7 pages.
"PCT International Preliminary Report on Patentability", PCT/US2006/18017, Apr. 15, 2008, 7 pages.
"Office Action", for U.S. Appl. No. 11/478,753, mailed Oct. 23, 2008, 14 pages.
Susan B. Klein, "Status of the Proton Therapy Project at IUCF and the Midwest Proton Radiotherapy Institute", AIP Conference Proceedings, Aug. 26, 2003—vol. 680, pp. 1081-1085.
A. N. Schreuder and A. Muller, "Development of a patient positioning system for high precision radiotherapy", Dec. 28, 2004, 4 pages.
PCT Search Report, PCT/US05/11469 filed Apr. 5, 2005, mailed Mar. 26, 2007.
PCT Written Opinion of the International Searching Authority, PCT/US05/11469 filed Apr. 5, 2005, mailed Mar. 26, 2007.
PCT International Preliminary Report on Patentability, PCT/US2005/011469 filed Apr. 5, 2005, mailed Apr. 26, 2007.
Linear Accelerators (5 pages), Sep./Oct. 2003, from Imaging Technology News, Sep./Oct. 2003, vol. 43, No. 5, www.ITNonline.net, + Cover page, Table of Contents (2 pages), 7 pages total.
Final Office Action for U.S. Appl. No. 11/129,122 mailed May 26, 2010, 19 pages.
Final Office Action for U.S. Appl. No. 11/129,122 mailed Mar. 31, 2010, 23 pages.
Office Action for U.S. Appl. No. 11/129,122 mailed Oct. 7, 2009, 35 pages.
Final Office Action for U.S. Appl. No. 11/478,753 mailed Oct. 23, 2008, 14 pages.
Office Action for U.S. Appl. No. 11/478,753 mailed May 29, 2008, 20 pages.
Office Action for U.S. Appl. No. 11/478,753 mailed Nov. 30, 2007, 15 pages.
Advisory Action for U.S. Appl. No. 11/478,753 mailed Aug. 21, 2007, 5 pages.
Final Office Action for U.S. Appl. No. 11/478,753 mailed Jun. 12, 2007, 17 pages.
Office Action for U.S. Appl. No. 11/478,753 mailed Dec. 18, 2006, 24 pages.
Notice of Allowance for U.S. Appl. No. 10/687,860 mailed Apr. 5, 2006, 9 pages.
Final Office Action for U.S. Appl. No. 10/687,860 mailed Jan. 24, 2006, 18 pages.
Office Action for U.S. Appl. No. 10/687,860 mailed May 31, 2005, 19 pages.

\* cited by examiner

PATIENT POSITIONING ASSEMBLY

RELATED APPLICATION

This is a continuation of U.S. patent application Ser. No. 10/881,315, filed on Jun. 30, 2004, now U.S. Pat. No. 7,860,550 which claims the benefit of U.S. Provisional Application Ser. No. 60/560,318, filed on Apr. 6, 2004, the entire contents of which are incorporated by reference. This application is related to U.S. application Ser. No. 10/687,860, now U.S. Pat. No. 7,154,991, filed Oct. 17, 2003, co-pending U.S. application Ser. No. 11/129,122, filed May 13, 2005, abandoned U.S. patent application Ser. No. 11/478,753, filed on Jun. 29, 2006, and co-pending U.S. application Ser. No. 12/793,467, filed on Jun. 3, 2010.

FIELD OF THE INVENTION

The present invention relates to a patient positioning assembly for medical operations, more particularly, to a patient positioning assembly, which is capable of motion in at least five degrees of freedom.

BACKGROUND

The term radiosurgery refers to a procedure in which intense and precisely directed doses of radiation are delivered to a target region in a patient, in order to destroy tumorous cells or otherwise treat the target region. The term radiotherapy refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgical session. For convenience, the term "radiosurgery" in this application shall henceforth mean "radiosurgery and/or radiotherapy." Both radiotherapy and radiosurgery are referred to herein as "therapeutic radiation treatments."

In radiosurgery, it is necessary to determine with precision the location of the target region (and surrounding critical structures) relative to the reference frame of the treatment device. It is also necessary to control the position of the radiation source so that its beam can be precisely directed to the target tissue while minimizing irradiation of surrounding healthy tissue.

To affect such beam position control, a frameless stereotactic radiosurgery system has been developed, which implements image-guided radiosurgery using a robot. An image-guided robotic system provides the requisite beam position control for accurate delivery of therapeutic radiation, while eliminating the need for rigid stereotactic frames. Such image-guided robotic systems typically include a treatment beam generator, for example a treatment x-ray source, mounted onto a robot, and a controller. The treatment x-ray source provides precisely shaped radiation beams to provide the required radiation dose and dose distribution. Using pre-treatment scan data, as well as treatment planning and delivery software, the controller acquires information regarding the pre-treatment position and orientation of the treatment target region. The patient is usually placed on a support device, such as a couch or a table. During treatment, an imaging system repeatedly measures the position and orientation of the target relative to the treatment x-ray source. Prior to the delivery of radiation at each delivery site, the controller directs the robot to adjust the position and orientation of the treatment x-ray source, in accordance with the measurements made by imaging system, so that the requisite dose of the treatment beam can be applied to the treatment target within the patient.

Accordingly, it is desirable to provide a patient positioning assembly that includes a dynamic motion control mechanism for controlling the motion of the support device, so that the position and orientation of the support device can be adjusted as necessary.

SUMMARY OF THE INVENTION

A robotic patient positioning assembly is provided for adjusting patient position during therapeutic radiation treatment using a therapeutic radiation treatment system, for example, an existing gantry-based linac system or a robot-based linac system (e.g. the CyberKnife® radiosurgery system, developed by Accuray, Inc.). An exemplary robot-based therapeutic radiation treatment system includes a robot having an articulated arm assembly, an treatment x-ray source mounted at one end of the arm assembly, an imaging system and a patient positioning subsystem.

The robotic patient positioning assembly (robot couch assembly) includes: 1) a support device (robot couch), which includes a supporting means controlled by a robot, for supporting and moving the patient during treatment; and 2) a sensor system for detecting the position of the robot couch. The robotic patient positioning assembly may further include a controller for controlling the motion of the robotic patient positioning assembly. The controller is operatively connected to and communicates with the sensor system of the robot couch assembly, and is adapted to calculate the position of the robot couch relative to the treatment room or other predefined treatment coordinate system based on the data received from the sensor system. The controller may also be adapted for controlling the motion of the robot couch in a way that the treatment target within the patient's anatomy remains properly aligned with respect to the treatment beam source throughout the treatment procedure.

In one preferred form, the controller is also connected to and communicates with the therapeutic radiation treatment system. The controller receives pre-treatment scan data representative of one or more pre-treatment scans of a treatment target within the patient. The pre-treatment scans show the position and orientation of the target with respect to a pre-treatment coordinate system. The controller receives from the imaging system image data representative of near real time images of the target. The image data contain information regarding the near real time position and orientation of the target with respect to a treatment coordinate system. The treatment coordinate system and the pre-treatment coordinate system are related by known transformation parameters.

The sensor system for detecting the position of the robot couch is preferably a resolver-based sensor system, or an inertial sensor attached to the robot couch for sensing the motions of the robot couch, or an infrared triangulation system, or a scanning laser system or an optical tracking system disposed within the treatment room for detecting the position of the robot couch relative to the treatment room or other treatment coordinate system. Correspondingly, the controller is loaded with software adapted for receiving information from the sensor system and calculating the position of the robot couch, so that the robot couch assembly including the control computer always knows the position of the robot couch.

The controller generates motion command signals for implementing corrective motions of the robot couch for aligning the target with respect to the radiation treatment source. In a robot-based linear accelerator (linac) system according to one preferred embodiment of the present invention, the corrective motions of the robot couch are coordinated with the motions of the treatment x-ray source, in a way as to maximize the workspace available to the radiosurgery apparatus. In this embodiment, the robot-implemented movements of the treatment x-ray source are complemented by the corrective motions of the robot couch, so that the relative motion between the treatment x-ray source and the robot couch ensures the delivery of the desired radiation pattern throughout the target region.

The controller of the robot couch assembly may be programmed to automatically or periodically calibrate the robot couch position with respect to the therapeutic radiation source.

In another embodiment, the corrective motions of the robot couch accommodate for various patient motions, such as breathing, coughing, sneezing, hiccupping, heartbeat, and muscular shifting.

The controller includes at least one user interface unit for enabling the user to interactively control the corrective motions of the robot couch, by implementing one or more user-selectable functions.

The robot couch is capable of motion in at least three degrees of freedom, namely three translational degrees of freedom (x-, y-, and z-). Preferably, the robot couch is capable of motion in all six degrees of freedom, namely three translational degrees of freedom plus three rotational degrees of freedom (roll-, pitch-, and yaw-rotations). The motion command signal, generated by the controller, thus controls corrective motions of the robot couch in at least three, and preferably six, degrees of freedom. In one form of the invention, the position of the robot couch with respect to the treatment system is known, so that coordinated movements may be effected. For example, both the robot couch and the treatment system can be referenced to a common (or "room") coordinate system.

In one preferred embodiment, the robot couch is provided with an at least two directions loading mechanism, which, in operation, can load or unload the patient in horizontal manners and vertical manners. The robot couch includes a supporting table, which, in a vertical loading manner, is preferably positioned oblique to the horizontal plane, for example at about 110 degrees with respect to the horizontal plane. After the patient is secured on the supporting table, the robot couch positions the patient to the treatment position. In one preferred form, the top surface of the supporting table is provided with a patient specific mold, which is customized to fit the body curve of the patient. In another preferred form, one end of the supporting table is provided with a footplate for supporting the patient's feet in vertical loading manners. In yet another preferred embodiment, the robot couch is provided with a chair-like supporting device, and the robot couch is adapted to provide a sitting position for loading and/or unloading, and/or for treating the patient.

In a further preferred embodiment, the supporting table is made of a radiolucent material so that the patient could be imaged through the supporting table. An exemplary imaging system that can be used with the positioning assembly and the linac system includes two x-ray imaging sources, power supplies associated with each x-ray imaging source, one or two imaging detectors, and a control computer. The x-ray sources are nominally mounted angularly apart, preferably about 90 degrees apart, and aimed through the iso-center (the patient) toward the detector(s). However, a single source that is moved between two positions could also be used. A single large detector may be used that would be illuminated by each x-ray source. In the single detector imaging system, the two x-ray sources may be positioned apart at an angle less than 90 degrees to keep both images on the single detector surface. The detector(s) is preferably placed below the iso-center, e.g., on the floor, on the top surface of the supporting table, or underneath the supporting table, and the x-ray sources are positioned above the iso-center, e.g. the ceiling of the treatment room, to minimize magnification of the images and therefore the required size of the detector. In an alternative form, the positions of the x-ray sources and the detector(s) can be reversed, e.g. the x-ray sources below the iso-center and the detector(s) above the iso-center. In another preferred embodiment, due to the constrained swing of the gantry of the treatment system, and to reduce the magnification effects, the detector(s) may be arranged in a manner such that they move into position for imaging while the gantry is positioned in a way that does not interfere with the imaging system, and then move out of the way during delivery of the therapeutic beam.

The detector(s) generates the image information and sends it to the controller. The controller performs all the imaging calculations to determine the patient's position with respect to the desired treatment position and generate corrections for at least five degrees of freedom. The corrections could be automatically applied to the patient positioning system to automatically align the patient, and/or be sent to the user interface for a user to manually adjust the patient's position relative to the therapeutic radiation source.

DETAILED DESCRIPTION

A robotic patient positioning assembly (robot couch assembly), is provided for adjusting patient position and orientation during medical operations. The patient positioning assembly according to the present invention is adapted for use with existing gantry-based (iso-centric) treatment systems or frameless, image-guided robot-based therapeutic radiation treatment systems, such as the CyberKnife® radiosurgery system, developed by Accuray, Inc., or other types of medical operation systems.

Figure 1:
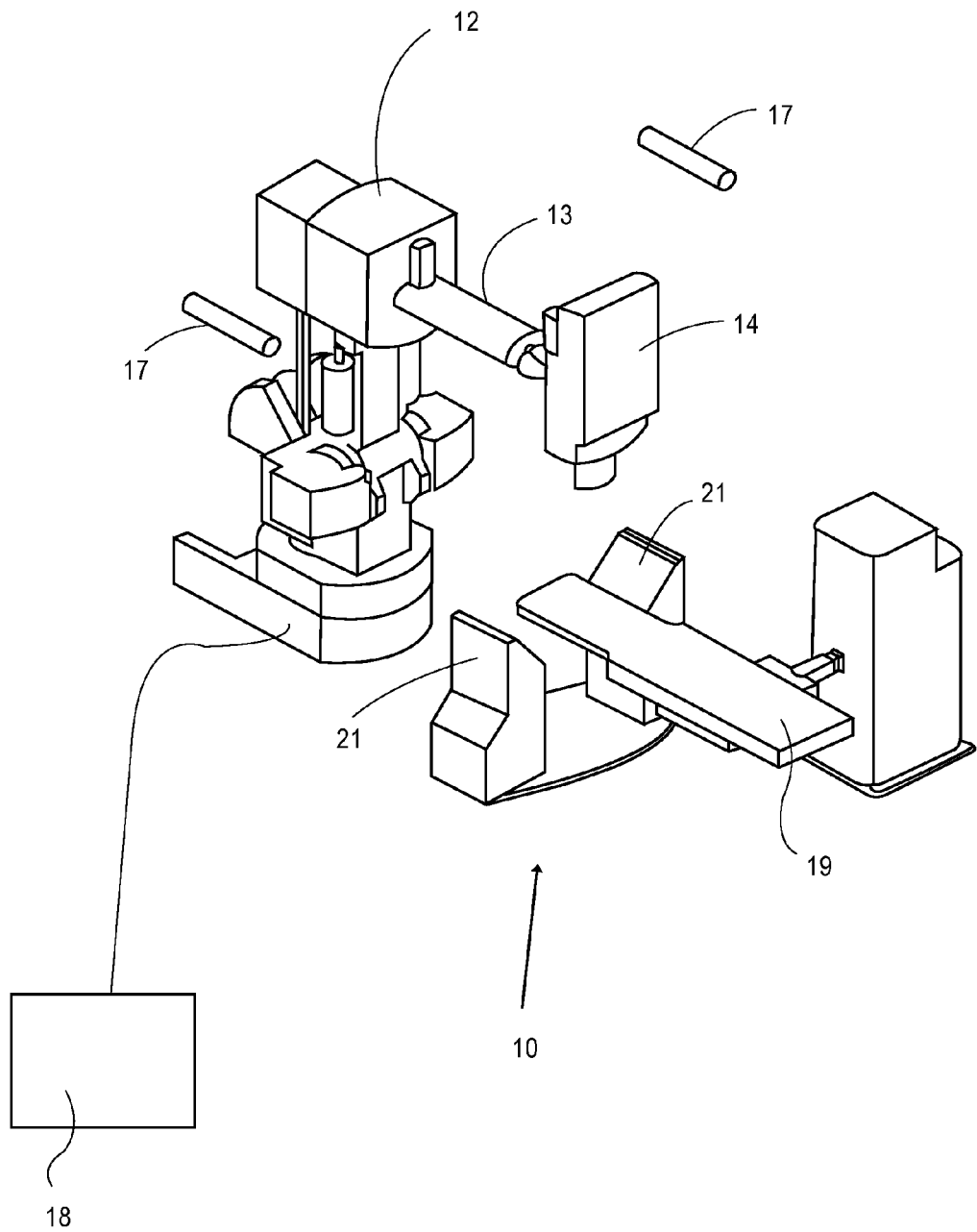
FIG. 1 schematically illustrates the CyberKnife® frameless radiosurgery system, known in the prior art.

FIG. 1 schematically illustrates the CyberKnife® radiosurgery system 10, known in the art. In overview, the radiosurgery system 10 includes: a robot 12, having an articulated arm assembly 13; a therapeutic radiation source 14, mounted at a distal end of the articulated arm assembly 13, for selectively emitting therapeutic radiation; an x-ray imaging system; and a controller 18. In the illustrated embodiment, the therapeutic radiation source 14 is an x-ray linear accelerator ("linac"). The x-ray imaging system generates image data representative of one or more near real time images of the target. The x-ray imaging system includes a pair of diagnostic x-ray sources 17, and a pair of x-ray image detectors (or cameras) 21, each detector located opposite an associated one of the x-ray sources 17. A patient support device (or treatment table) 19 supports the patient during treatment, and is positioned between the two x-ray cameras 21 and their respective diagnostic x-ray sources 17.

The imaging system generates, in near real time, x-ray images showing the position and orientation of the target in a treatment coordinate frame. The controller 18 contains treatment planning and delivery software, which is responsive to pre-treatment scan data CT (and/or MRI data, PET data, ultrasound scan data, and/or fluoroscopy imaging data) and user input, to generate a treatment plan consisting of a succession of desired beam paths, each having an associated dose rate and duration at each of a fixed set of treatment positions or nodes. In response to the controller's directions, the robot 12 moves and orients the x-ray linac 14, successively and sequentially through each of the nodes, while the x-ray linac 14 delivers the required dose as directed by the controller 18. The pre-treatment scan data may include, for example, CT scan data, MRI scan data, PET scan data, ultrasound scan data, and/or fluoroscopy imaging data.

Prior to performing a treatment on a patient with the CyberKnife® radiosurgery system, the patient's position and orientation within the frame of reference established by the x-ray imaging system 16 of the Cyberknife® radiosurgery system must be adjusted to match the position and orientation that the patient had within the frame of reference of the CT (or MRI or PET or fluoroscopy) scanner that provided the images used for planning the treatment. It is desirable that this alignment be performed to within tenths of a millimeter and tenths of a degree for all six degrees of freedom.

Although the robot-based radiosurgery system has been described in detail in the above description and will be used as examples for using with the robotic patient positioning system, a person skilled in the art should understand that the present invention also can be used with the existing gantry-based (iso-centric) treatment systems. It is also should be appreciated that the robotic patient positioning assembly according to the present invention can be used for other medical applications, for example, as an operating room (OR) table, or as a supporting device in CT scanning or in MRI process, and the like.

Figure 2:
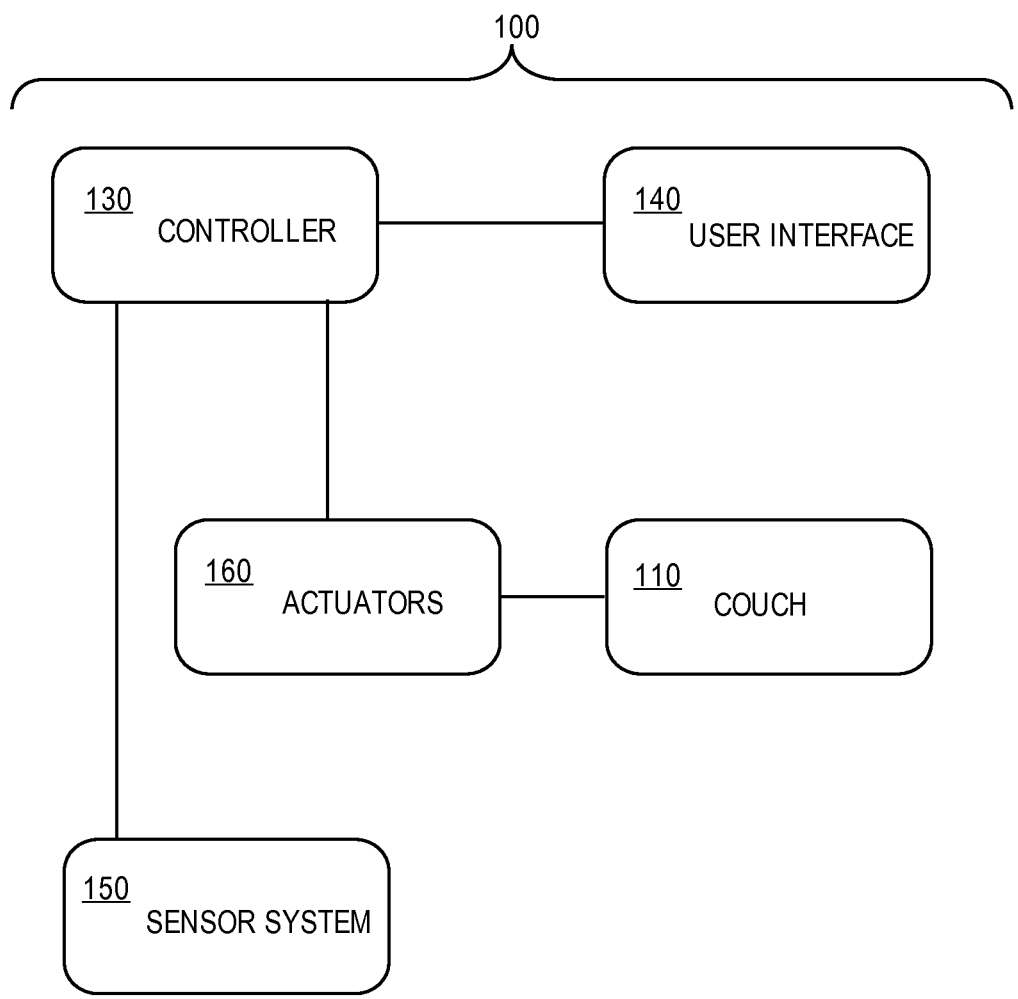
FIG. 2 is a schematic block diagram of a patient positioning assembly for therapeutic radiation treatment.

FIG. 2 provides a schematic block diagram of a robotic patient positioning assembly 100 that adjusts patient position under computer control, during radiation treatment, according to one preferred embodiment of the present invention. In overview, the robotic patient positioning assembly (robot couch assembly) 100 includes: 1) a support device (robot couch) 110, which includes a supporting means 112 controlled by a robot 114, for supporting the patient during treatment; and 2) a sensor system 150 for detecting the position of the robot couch 110. The robot couch assembly 100 may further include a controller 130 including a control computer. The controller 130 is operatively connected to and communicates with the sensor system 150 of the robot couch assembly 100, and is adapted to calculate the position of the robot couch 110 relative to the treatment room or other predefined treatment coordinate system based on the data received from the sensor system 150. The controller 130 may also be adapted for controlling the motion of the support device 110 in a way that the treatment target within the patient's anatomy remains properly aligned with respect to the treatment beam source throughout the treatment procedure. In one preferred form, the controller 130 is also connected to and controls the therapeutic treatment system.

In the illustrated embodiment, the supporting means 112 is a treatment table, although in other embodiments, other types of support devices (such as a chair or bench) may be used. The supporting table 112 is capable of motion in at least three degrees of freedom, namely three translational degrees of freedom (x-, y-, and z-). Preferably, the table is capable of motion in all six degrees of freedom, namely three translational degrees of freedom plus three rotational degrees of freedom (roll-, pitch-, and yaw-rotations). The motion command signal, generated by the controller 130, thus controls corrective motions of the table in at least three, and preferably six, degrees of freedom.

Figure 3:
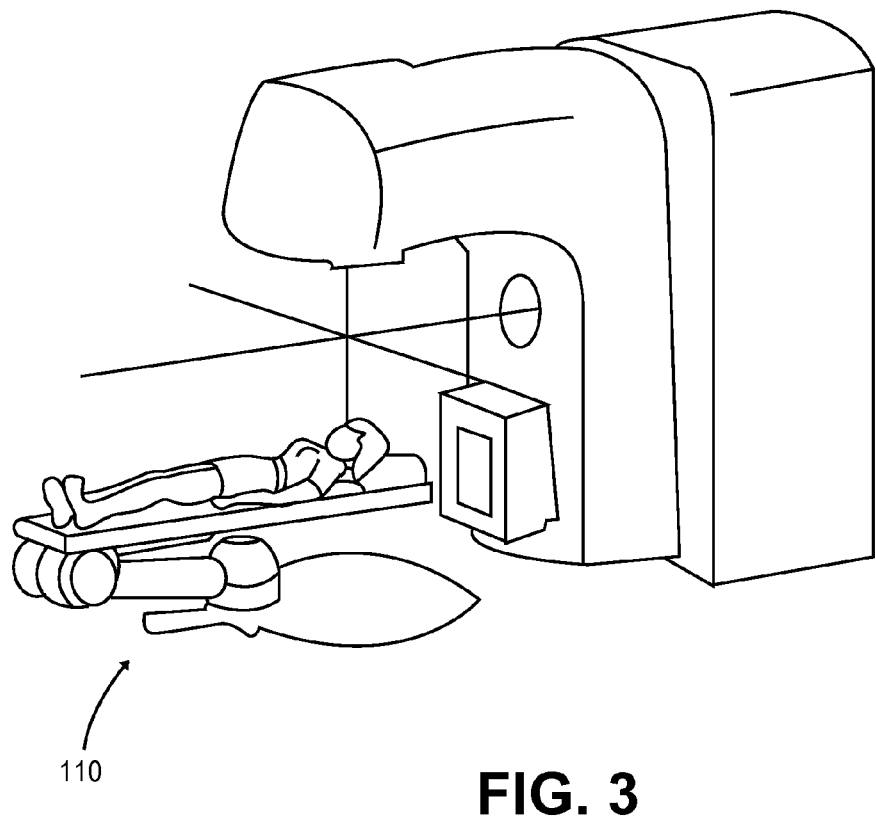
FIG. 3 is a perspective view of a patient positioning assembly for therapeutic radiation treatment, showing the assembly loading/unloading a patent in a horizontal manner.
Figure 4:
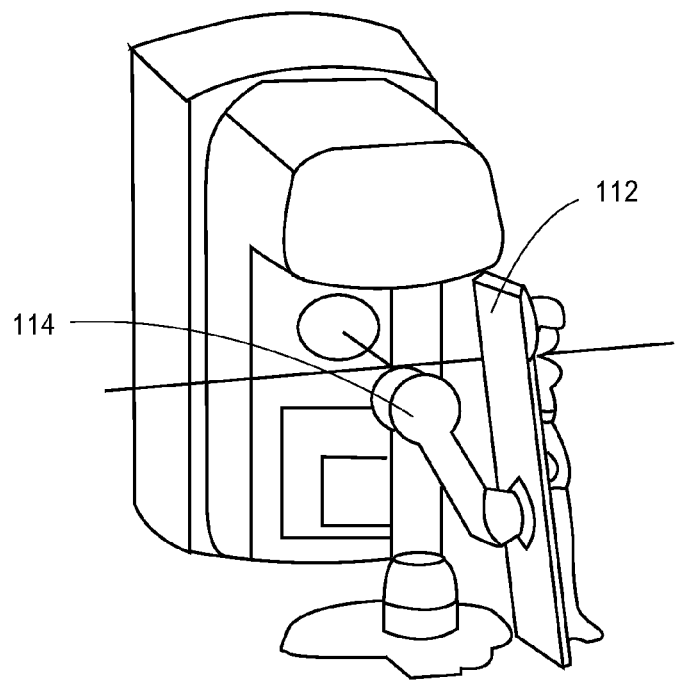
FIG. 4 is a perspective view of a patient positioning assembly for therapeutic radiation treatment, showing the assembly loading/unloading a patent in a vertical manner.
Figure 5:
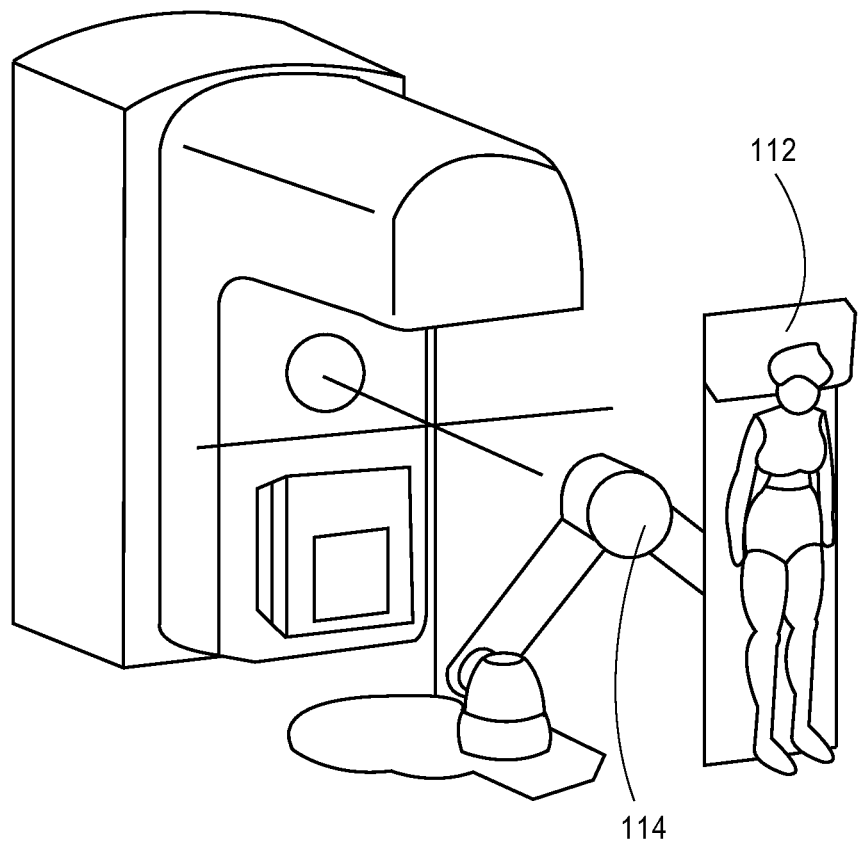
FIG. 5 is a perspective view of a patient positioning assembly for therapeutic radiation treatment, showing the assembly loading/unloading a patent in another vertical manner.
Figure 6:
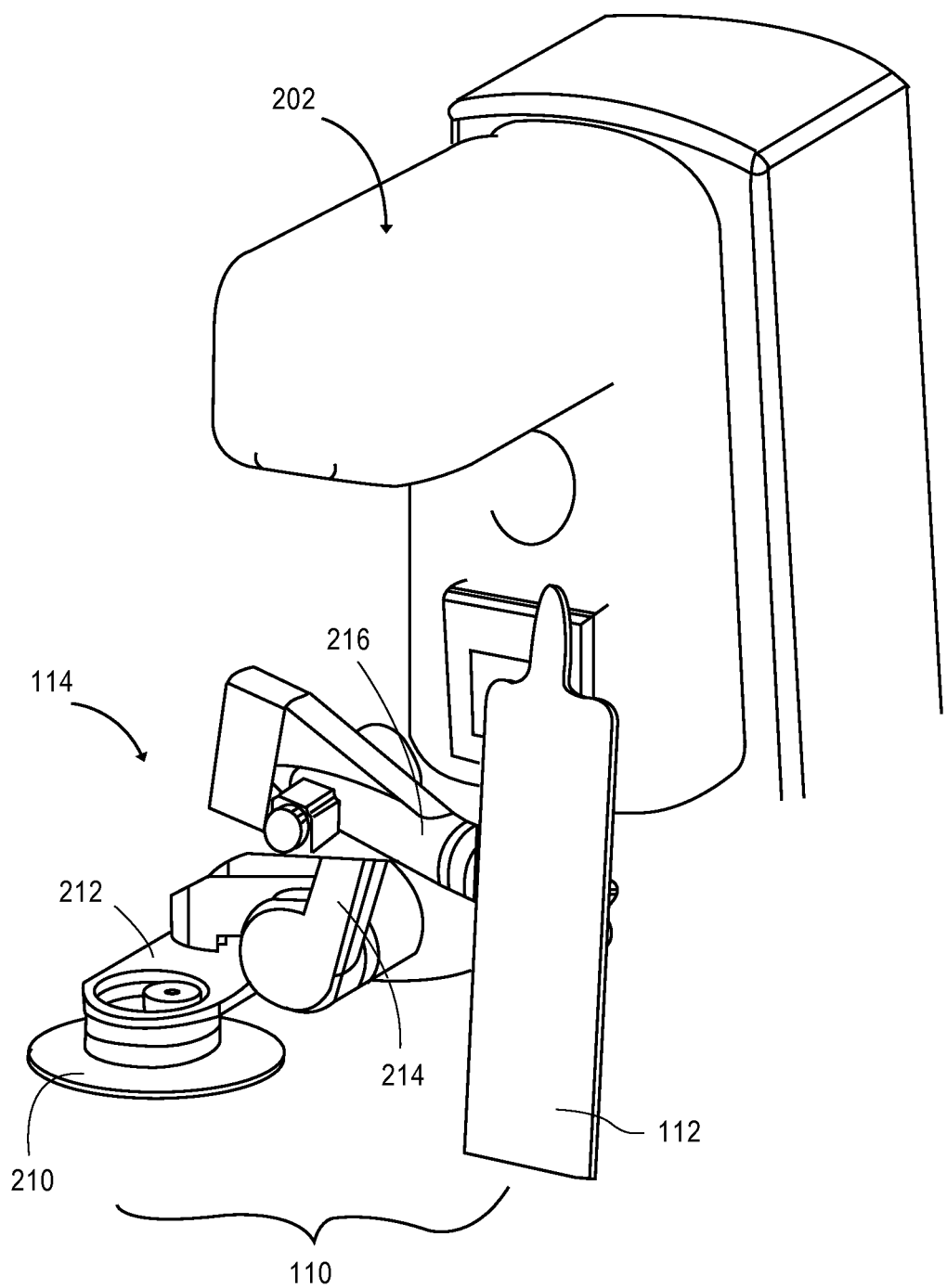
FIG. 6 is a perspective view of a patient positioning assembly for therapeutic radiation treatment, showing another vertical loading/unloading position of a treatment table.
Figure 7:
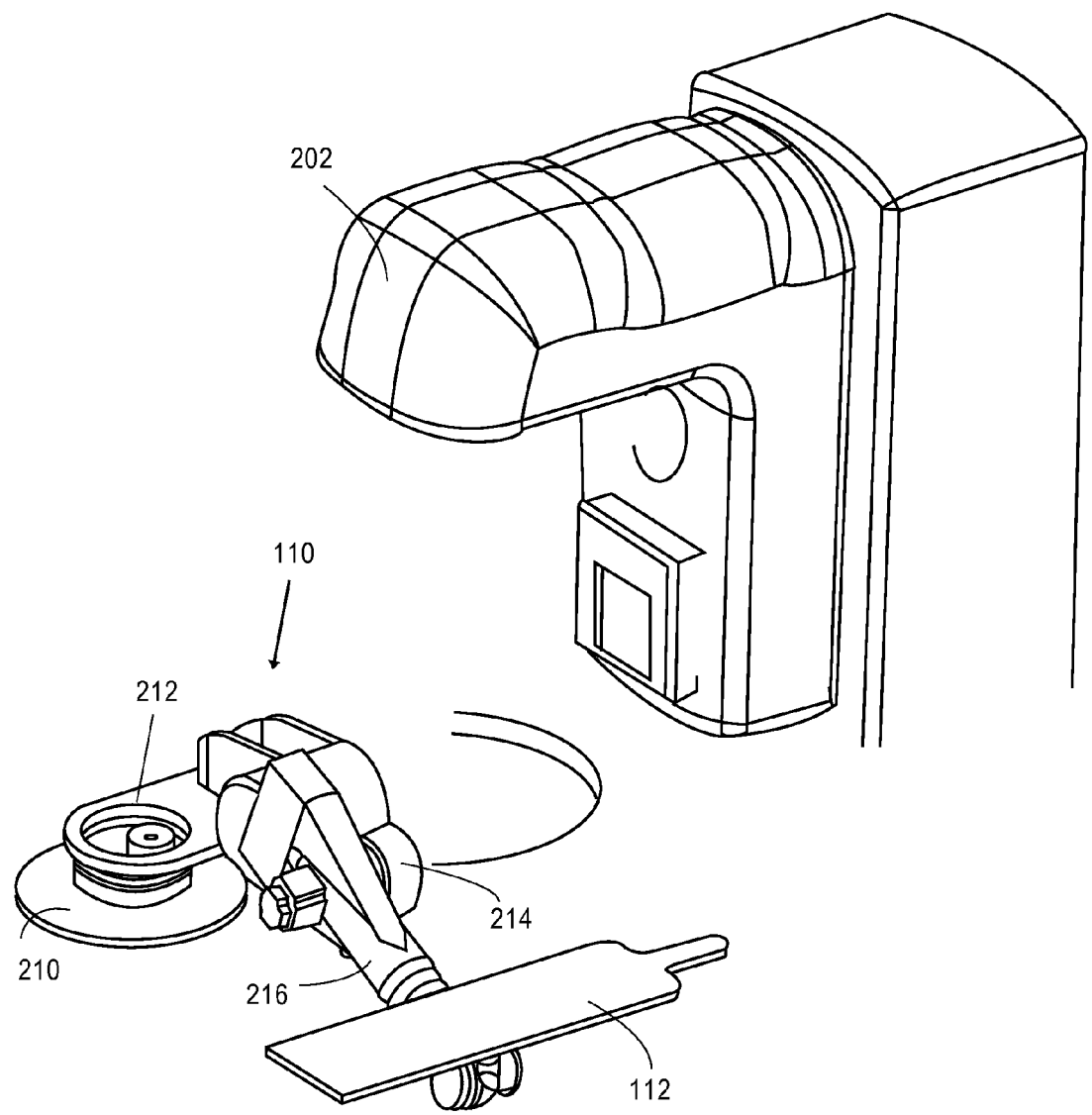
FIG. 7 is a perspective view of a patient positioning assembly for therapeutic radiation treatment, showing an ultra-low loading/unloading position of the treatment table.
Figure 8:
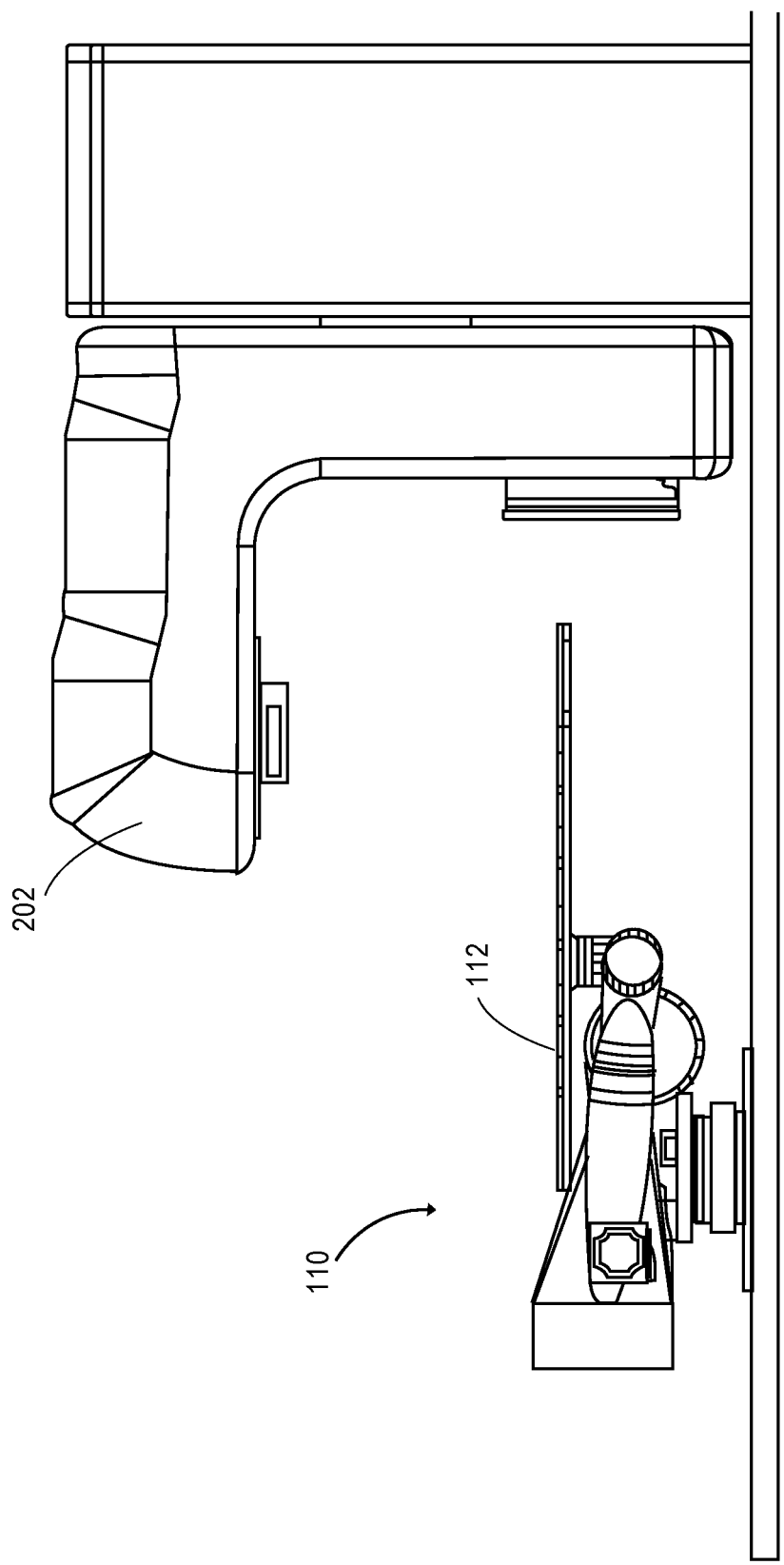
FIG. 8 is a perspective view of a patient positioning assembly for therapeutic radiation treatment, showing a normal treatment position of the treatment table.

In one preferred embodiment, the support device 110 is provided with a loading mechanism, which, in operation, can load or unload the patient in horizontal manners, as shown in FIG. 3, and vertical manners as shown in FIGS. 4, 5, and 6. The supporting surface (top surface) of the table 112 is preferably positioned oblique to the horizontal plane, for example at about 110 degrees with respect to the horizontal plane as shown in FIG. 4, when the system loads a patient in a vertical manner. After the patient is secured on the supporting surface, the robot 114 positions the patient to the treatment position. In one preferred form, the supporting surface of the robot-controlled table 112 is provided with a patient specific mold, which is customized to fit the body curve of the patient. In another preferred form, one end of the supporting table is provided with a footplate for supporting the patient's feet in vertical loading manners. Alternatively, the support device 110 may also provide ultra-low loading/unloading positions as shown in FIG. 7, sitting loading/unloading positions, and other loading/unloading positions which are set for the convenience of particular patients. FIG. 8 shows a normal treating position of the treatment table 112.

The robot 114 includes one or more table motion actuators 160 for moving the table 112, in accordance with directions from the controller 130. The controller 130 and the sensor system 150 ensure that the table does not collide with obstacles during table motion.

FIGS. 6-8 illustrate an exemplary embodiment of the robot couch assembly together with a gantry-based linac treatment system 202. As shown in FIGS. 6-8, the robot 114 includes a base 210, a plate member 212, a first arm 214, and a second arm 216. The base 210 is secured on the floor of the treatment room during treatment. The plate member 212 is rotatably mounted on the base 210. A first end of the first arm 214 is rotatably connected to the plate member 214. A first end of the second arm 216 is rotatably connected to a second end of the first arm 214. The treatment table 112 is rotatably attached to a second end of the second arm 216 at approximately a middle portion of the treatment table 112 such that the treatment table 112 is permitted to rotate about at least one, preferably three orthogonal axes. The arrangement of the base 210, the plate member 212, the first arm 214, and the second arm 216 provides the treatment table 112 with six degrees of freedom. The robot couch assembly 100 can position the patient on the treatment table in any place in the desired treatment area and can provide any loading/unloading position for a particular patient.

Figure 11:
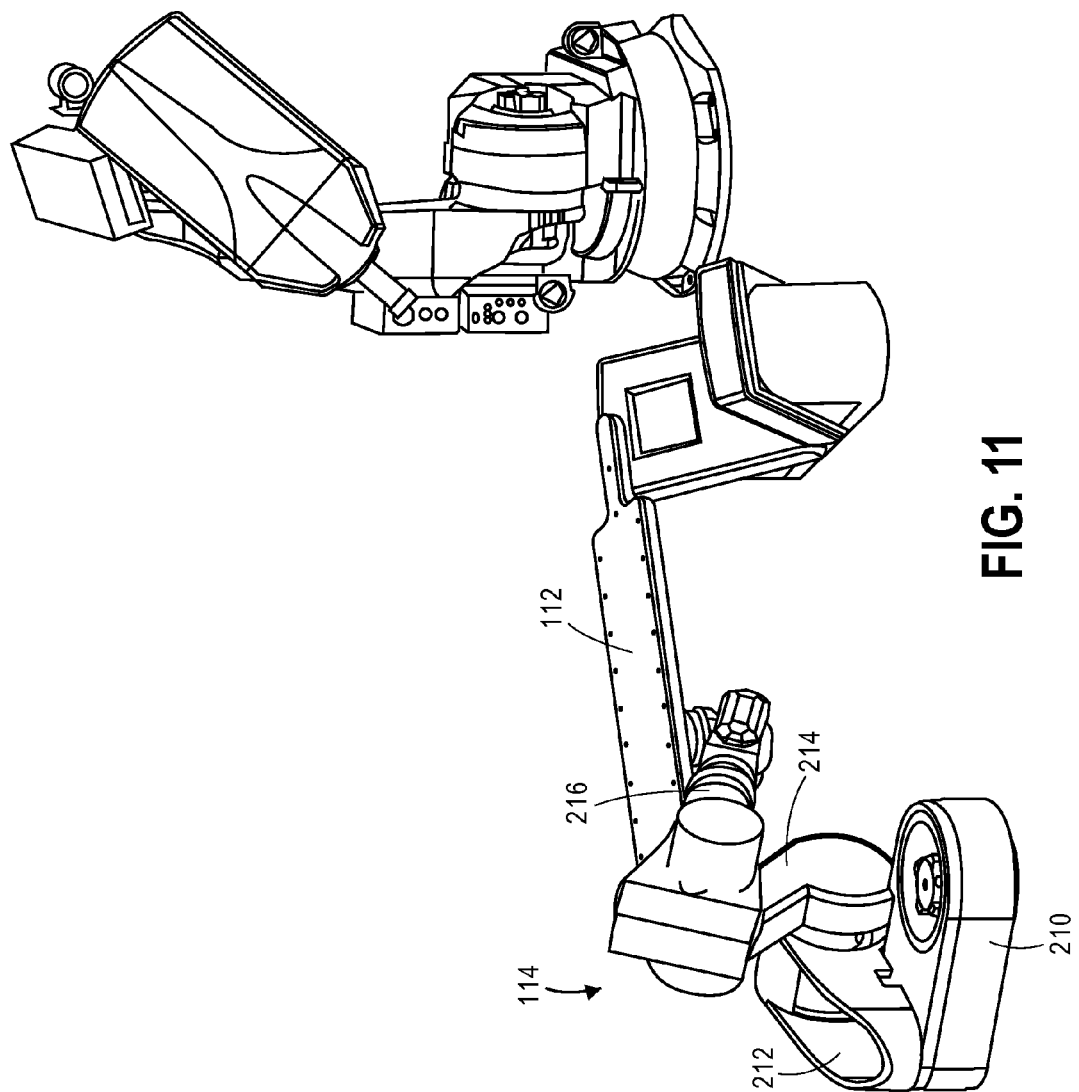
FIG. 11 illustrates a perspective view of a patient positioning assembly together with the CyberKnife® radiosurgery system.
Figure 12:
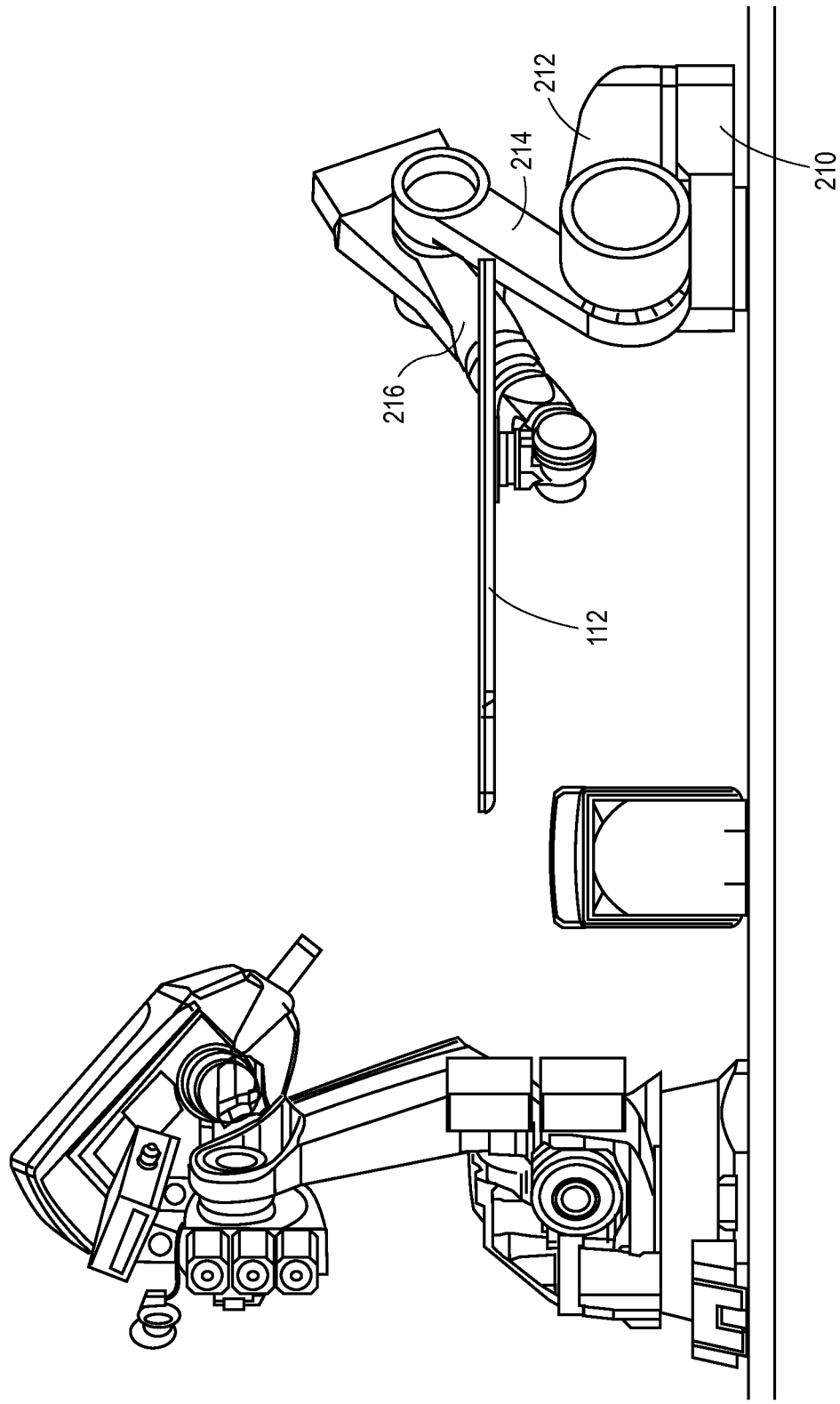
FIG. 12 illustrates a perspective side view of a patient positioning assembly together with the CyberKnife® radiosurgery system.

FIGS. 11 and 12 illustrate another exemplary embodiment of the robot couch assembly together with the CyberKnife® radiosurgery system. The robot couch assembly in FIGS. 11 and 12 are substantially the same as the robot couch assembly illustrated in FIGS. 6-8, except that in the robot couch assembly in FIGS. 11 and 12, the base 210 is rotatably mounted on the floor, or alternatively, the base 210 is rotatably mounted to a plinth, which is secured on the floor, or within or under the floor.

A person skilled in the art should appreciate that more rotatable and/or slidable sections, for example, a third arm, can be added to the robot couch assembly to obtain more flexibility and a greater reach of the robot couch. Alternatively, the robot couch assembly can include less sections than the robot couch assembly shown in FIGS. 6-8 and FIGS. 11 and 12, for example, including only one arm section instead of two arms. These specific forms should be considered equivalent to the present invention. The rotation and other movements of the robot couch assembly can be controlled manually and/or by a computer controller.

The sensor system 150 for detecting the position of the support device 110 is preferably a resolver-based sensor system, or an inertial sensor attached to the robot couch for sensing the motions of the robot couch, or an infrared triangulation system, or a laser scanning system, or an optical tracking system disposed within the treatment room for detecting the position of the support device 110 relative to the treatment room or other treatment coordinate system. An exemplary laser scanning system may scan the treatment room approximately 60×/sec to determine the position of the robot couch 110. The laser scanning system may include devices performing a single plane scanning, or two-plane scanning, or multiple-plane scanning. Correspondingly, the controller 130 is loaded with software adapted for receiving information from the sensor system 150 and calculating the position of the robot couch 110, so that the robot couch assembly 100 including the control computer always knows the position of the robot couch 110. The controller 130 may be programmed to automatically or periodically calibrate the robot couch with the therapeutic radiation source. In an alternate embodiment, the sensor system 150 includes a magnetic tracking system for tracking the position of the support device 110 relative to the treatment coordinate system. The magnetic tracking system preferably includes at least one transducer attached to the support device 110.

The communication links between the controller 130 and the robot couch assembly 100 (including the support device 110 and the sensor system 150) can be wired links or wireless links, with a bandwidth necessary for maintaining reliable and timely communications.

In one embodiment, the patient positioning assembly 100 further includes at least one user interface 140, including one or more user interface units that enables a user or operator to interactively participate in controlling the motion of the support device 110.

The controller 130 may include an input module for receiving 1) pre-treatment scan data representative of pre-treatment scans of the target, and 2) near real time image data representative of near real time images of the target. The pre-treatment scans show the position and orientation of the target with respect to the pre-treatment coordinate system. The near real-time images, taken by the imaging system under the command of the controller, show the position and orientation of the target with respect to the treatment coordinate system. The treatment coordinate system and the pre-treatment coordinate systems are related by known transformation parameters. The controller includes a TLS (target location system) processing unit that computes the position and orientation of the target in the treatment coordinate system, using the pre-treatment scan data, the near real time image data, and the transformation parameters between the pre-treatment coordinate system and the treatment coordinate system.

Since the robot couch assembly 100 including the controller 130 knows the position of the supporting device 110 through the sensor system 150 and the position of the treatment target through the near real time image data, and also knows the position of the iso-center of the linac system, the robot couch assembly 100, in one preferred form, is adapted to automatically position or periodically adjust the position of the treatment target to the iso-center of the linac. In one preferred form, the robot couch assembly 100 including the controller 130 is adapted to detect the misalignment of the treatment target with the iso-center of the linac system caused by patient's movement by comparing the position of the treatment target with the iso-center of the linac system, and adjust the position of the treatment target to align the target with the iso-center of the linac system.

During treatment, the patient's breath motions may cause displacement of the treatment target from the radiation source or the iso-center of the therapeutic radiation treatment system. In a further preferred form, the robot couch assembly 100 is programmed to compensate the displacement of the treatment target from the iso-center of the treatment system that would be caused by the breath motions of the patient by reverse synchronizing the movement of the robot couch with the breath motions of the patient, thereby maintaining the target aligned with the iso-center of the treatment system.

In one embodiment, the corrective motions of the supporting table 112, implemented by the motion command signals generated by the controller 130, compensate for various patient motions that the patient may undergo during treatment. These patient motions may include, but are not limited to, the following: respiratory motion; cardiac pumping motion of the patient's heart; sneezing, coughing, or hiccupping; and muscular shifting of one or more anatomical members of the patient.

In another preferred embodiment, the robot couch assembly 100 including the controller 130 is adapted to detect and accommodate changes in tumor geometry that may be caused by tissue deformation by comparing the near real time image with the pre-treatment image and repositioning the patient or the radiation source (in a robot-based treatment system), or adjusting treatment plan to rearrange the positions of the robot couch and the radiation source.

In one embodiment, in a robot-based treatment system, the controller 130 controls the motion of the treatment x-ray source 14, as well as the motion of the supporting table 112. In other words, the controller 130 controls the relative motion of the supporting table 112, with respect to the robot-implemented motion of the treatment x-ray source 14. In this way, the corrective motions of the table, implemented by the motion command signal from the controller 130, compensates for one or more motions of the treatment x-ray source implemented by the robot 12. In one embodiment, the combination of the motions of the supporting table 112 and the motions of the x-ray linac 14, are dynamically coordinated and controlled, so as to maximize the workspace available to the therapeutic radiation treatment system.

In a further preferred embodiment, the table 112 is made of a radiolucent material so that the patient could be imaged through the table 112. An exemplary imaging system that can be used with the patient positioning assembly and the linac system includes two x-ray imaging sources, power supplies associated with each x-ray imaging source, one or two imaging detectors, and a control computer. The x-ray sources are nominally mounted angularly apart, preferably about 90 degrees apart, and aimed through the iso-center (the patient) toward the detector(s). A single large detector may be used that would be illuminated by each x-ray source. In the single detector imaging system, the two x-ray sources may be positioned apart at an angle less than 90 degrees to keep both images on the single detector surface. The detector(s) is preferably placed below the iso-center, e.g., on the floor, on the supporting table 112, or underneath the supporting table 112, and the x-ray sources are positioned above the iso-center, e.g. the ceiling of the treatment room, to minimize magnification of the images and therefore the required size of the detector. In an alternative form, the positions of the x-ray sources and the detector(s) can be reversed, e.g. the x-ray sources below the iso-center and the detector(s) above the iso-center. In another preferred embodiment, due to the constrained swing of the gantry of the treatment system, and to reduce the magnification effects, the detector(s) may be arranged in a manner such that they move into position for imaging while the gantry is positioned in a way that does not interfere with the imaging system, and then move out of the way during delivery of the therapeutic beam.

The detector(s) generates the image information and sends it to the control computer (controller 130). The control computer performs all the imaging calculations to determine the patient's position with respect to the desired treatment position and generate corrections for at least five degrees of freedom. The corrections could be automatically applied to the patient positioning system to automatically align the patient, and/or sent to the user interface 140 for a user to manually adjust the patient's position relative to the therapeutic radiation source.

In a preferred embodiment, an anti-collision model may be embedded in the computer to ensure that the patient is not positioned in an orientation that might cause a collision between the patient's body and the linac gantry or other moving part.

The controller 130 includes software for establishing and maintaining a reliable communication interface with the support device 110. The software uses the interface specifications developed for the support device 110. The controller 130 further includes software for converting the patient position and orientation information from the imaging system to appropriate units of movement in the six degrees of freedom of motion capability of the table. The controller further includes software for providing a user interface to the treatment system user control console, to monitor and initiate the table motion to position the patient. The controller further includes software for detecting, reporting, and handling errors in communication or software control of the table.

The user interface 140 effects computer control of the six degrees of freedom of the robot-controlled table 112. In a particular embodiment, the user interface 140 includes: a bus interface for connecting the table 100 to the treatment system primary workstation; at least one user interface unit for allowing the user to interface with the controller to interactively control the table motion; and a hardware interface to the treatment system E-stop (emergency stop) circuitry. The bus interface may be an Ethernet bus interface that can be connected to the treatment system primary workstation. The hardware interface to the E-stop circuitry disables to computer-controlled table motions when any E-stop is engaged.

The E-stop mechanism is operable to stop computer-controlled motion of the table 112. In one embodiment, the "System E-stop" is an emergency lockout mechanism, capable of shutting down any and all radiation, and any and all motion. In other words, the "System E-stop" shuts down at least the following: 1) generation of therapeutic x-ray beams by the treatment x-ray source; 2) any motion of the treatment x-ray source and/or the robot; 3) any motion of the table; and 4) the imaging system.

The user interface allows the user or operator to interactively participate in controlling the motion of the table, by implementing one or more user-selectable functions. These user-selectable functions include, but are not limited to, the following: 1) a function that allows the user to power on the table, so that the acquisition of the position of the robot couch can be initiated; 2) a function that allows the user to activate the x-ray imaging system, so that the acquisition of near real time images of the target can be initiated; 3) a function for allowing the user to move the table to one or more pre-programmed loading positions, which facilitates the loading of the patient onto the table in a desired manner; 4) a function for allowing the user to move the table to a pre-programmed "TREAT" position, which is the default treatment position; 5) a function for displaying to the user the three translations and three rotations corresponding to the table corrective motions needed to adjust the target position, in accordance with the information from the near real time images; 6) a function for allowing the user to compare the translations and rotations with respective pre-specified limits for each translation and rotation; 7) a function for allowing the user to modify one or more of the pre-specified limits; and 8) a function for allowing the user to verify that the translations and rotations fall below the pre-specified limits, and thereupon activate the treatment x-ray source to initiate treatment delivery.

Figure 9:
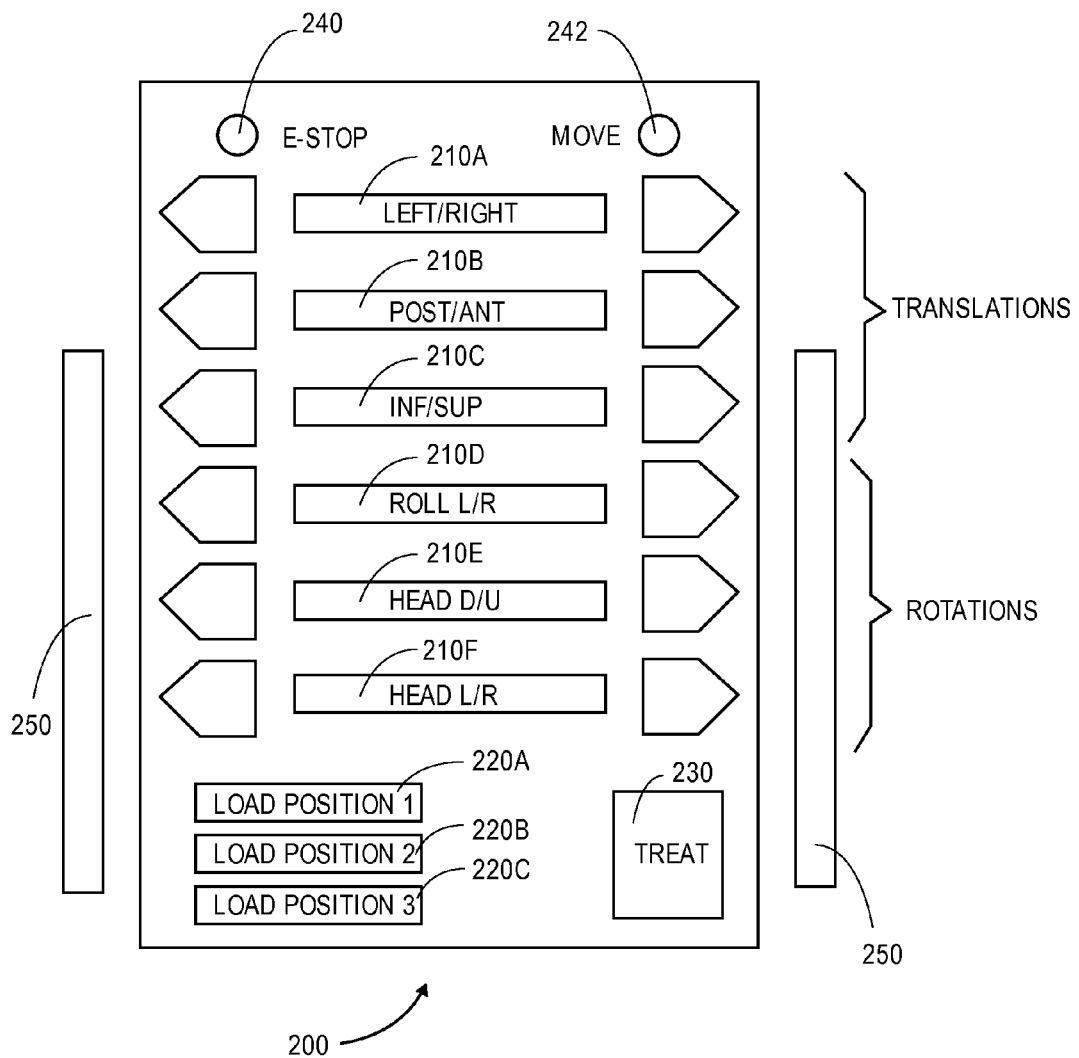
FIG. 9 is a schematic diagram of a handheld user interface unit, with remote control capabilities.

In a particular embodiment, the user interface unit is a remote control unit that provides a user with remote control capabilities for remote control of the motion of the support device 110. FIG. 9 is a schematic diagram of a handheld user interface unit 200, with remote control capabilities. In the illustrated embodiment, the user interface unit 200 is a handheld pendant, and includes a number of button icons respectively associated with these user-selectable functions. The handheld remote control unit 200 provides controls to manually adjust the patient's position, and status indicators related to the table motions.

In the illustrated embodiment, the handheld remote control unit 200 includes motion switches: six sets of axes motion control switches 210A-210F, three loading position switches 220A, 220B, and 220C, and a treat switch 230. The axes motion control switches provide bi-directional manual control of each degree of freedom via a pushbutton. The axes motion control switches cause movement of the desired axes (three translational axes: left/right (210A), posterior/anterior (210B), inferior (towards the feet)/superior (towards the head) (210C); three rotational axes: roll left/right (210D); head down/up (210E); head left/right (210F)) in the desired direction, as long as the switch is held down and motion is disabled. The loading switches 220A, 220B, and 220C each initiate a programmed motion, if motion is enabled, that causes the table to automatically move to the fully retracted, fully lowered loading position without any further operator action. Preferably, the three pre-programmed loading positions are the positions shown in FIGS. 3-5. In alternative embodiments, the controller may have more than three preprogrammed loading positions, and alternatively, a user may manually set a loading position for a patient through the handheld user interface 200 or a computer interface 300 illustrated in FIG. 10. The controller may store the loading position for a particular patient for future treatment. The treat switch 230 initiates a programmed motion, if motion is enabled, that causes the table to move to a position defined by the treatment computer and previously downloaded to the table.

The remote control unit 200 also includes a pair of motion enable switches 250. Depressing both switches enables all motion switches (axes motion control, loading positions, and treat), and overrides the System E-stop, if present, although it does not override any table E-stop switches. Releasing one or both of the enable switches while a programmed motion is occurring will cause that motion to stop.

The remote control unit 200 also includes a pair of status indicators 240 and 242, which are LEDs (light emitting diodes) that provide an indication of whether motions are enabled and being accepted. In the illustrated embodiment, the E-stop LED 240 is yellow when System E-stop is asserted, green when overridden by enable switches, and off when no System E-stop is asserted. The MOVE LED 242 is green whenever a switch is pushed and motion is enabled, flashing green when a programmed movement is occurring, and yellow when the table E-stop is engaged.

The remote control unit 200 may also include a GO TO switch (not shown), allowing the user to access stored locations. The remote control unit 200 may also include display capabilities (not shown), for example to display to the user the three translations and three rotations, or to display informational messages to the user. The remote control unit 200 may also include absolute and relative position display/input modes (not shown). In another preferred form, the remote control unit 200 may also include a switch for activating the sensor system 150 to initiate detecting the position of the robot couch.

Figure 10:
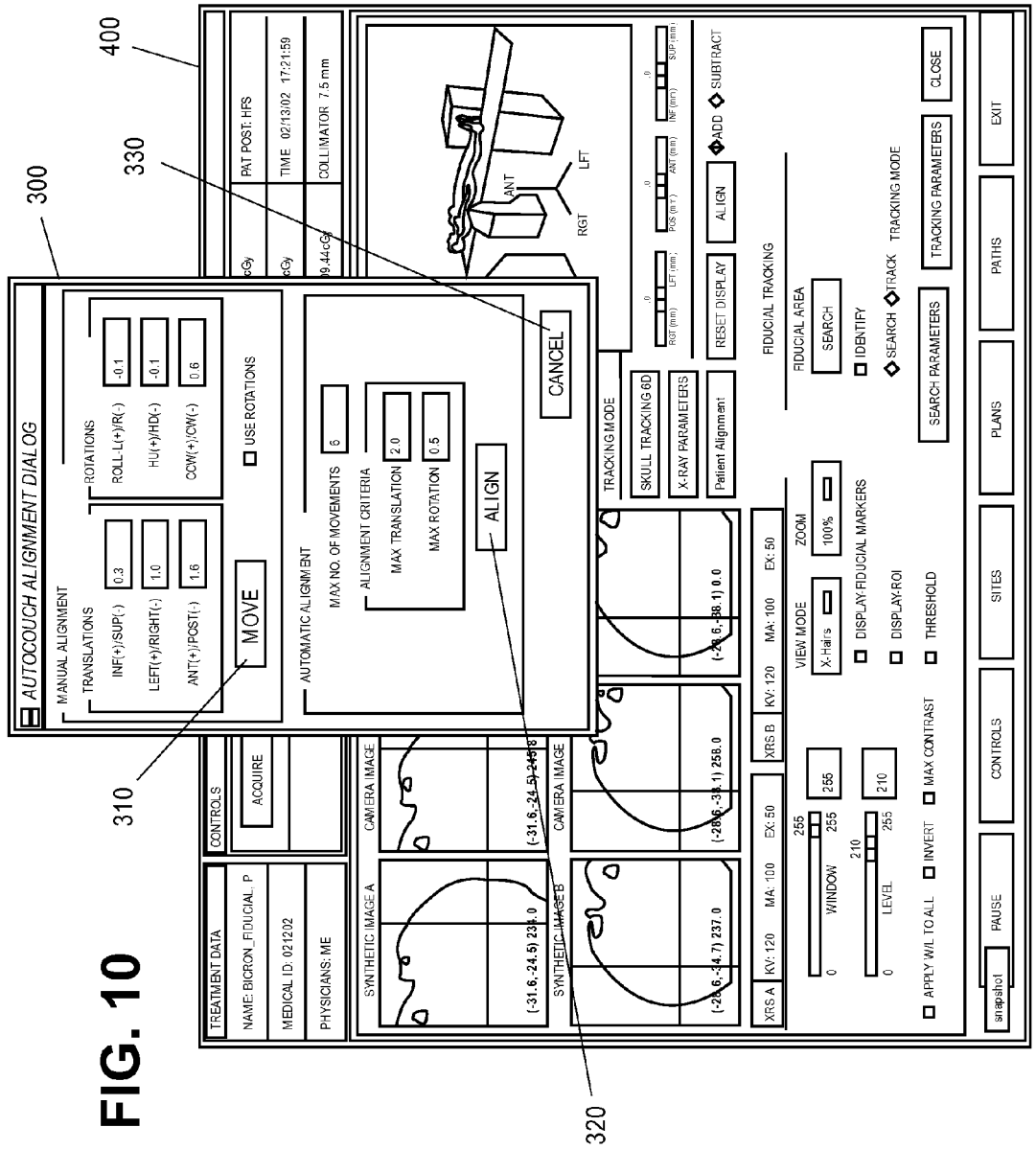
FIG. 10 illustrates an exemplary user interface screen, launched onto a treatment delivery display screen.

One or more user interface screens on the user control console of the primary workstation of the Cyberknife® radio surgery system, allows the user to inspect, initiate, and interactively control the table motion to position the patient. FIG. 10 illustrates an exemplary user interface screen 300, launched into a treatment delivery screen 400 of the primary workstation. In the illustrated embodiment, the user interface screen 300 provides to the user an integrated table position display, and table motion control capabilities. The user interface screen 300 provides sub-options to adjust translations only, or rotations only or all the six degrees of freedom available together.

In one embodiment, the user interface screen 300 includes button icons that allow the user to activate the sensor system 150 to detect the position of the robot couch.

In the illustrated embodiment, an ALIGN COUCH button in the treatment delivery screen 400 launches the user interface screen 300. The user interface screen 300 includes a number of fields, with different functions. These fields include translation and rotation fields, which are initially filled with the table corrective motions returned by the TLS unit of the controller. If no valid table corrective motions are available, these fields are left blank. The translation and rotation fields are editable.

In the illustrated embodiment, the user interface screen 300 includes a MOVE button 310, an "AUTO ALIGN" button 320, and a "CANCEL" button 330. The "MOVE" button 310 moves the table by the amount of translations and rotations indicated. If the "Apply rotation" field is unchecked, the table is moved only in translational axes. The "AUTO ALIGN" button 320 initially moves the table by the amount of translations and rotations indicated, and proceeds to acquire images and correct table positions automatically until pre-specified "Auto align limits" are satisfied. This means that the translations and rotations are below the pre-specified limits, or the number of images indicated are taken. The "Auto align limits" fields are filled in from a system configuration file, but can be edited. The "CANCEL" button 330 will return to the Patient Alignment interface.

In one embodiment, the user interface screen 300 includes button icons that allow the user to adjust imaging parameters, such as the intensity, energy, and duration of the x-rays in the imaging beams generated by the imaging system; the number of near real time images to be acquired; the selection and de-selection of fiducials; and rigid body parameters.

In operation, an approximate treatment location for the patient is computed, as part of the treatment planning process. When the treatment plan is loaded into the controller, the approximate treatment location is downloaded into the treatment table. The operator positions the patient on the table, and applies any restraining devices. The operator then presses the "Treat" button in the handheld user interface unit 200 (shown in FIG. 9), and the table automatically moves to bring all of its degrees of freedom to the stored positions. Alternatively, the "Treat" command could also be issued from the computer interface screen. The number of axes to move simultaneously may be limited by design to ensure that power demands are not excessive and that the patient is comfortable with the number of simultaneous motions taking place.

The operator then exits the treatment room and using the user interface screen 300 (shown in FIG. 10) on the workstation or dedicated control panel, commands the system to align the patient to within desired tolerances. The user interface screen allows the user to enter parameters such as the maximum number of near real time images to take during the alignment process, and the desired tolerances for position and orientation. The user interface screen also allows the errors associated with each image to be displayed.

After obtaining a satisfactory alignment, the radiosurgery system is commanded to begin treatment. As part of the treatment, near real time images are obtained periodically by the imaging system, to ensure that the patient doesn't move during the treatment. If the patient does move, the operator can cause treatment delivery to be paused, and the patient to be realigned, by effecting appropriate corrective motions of the table. At the conclusion of the treatment, the operator reenters the treatment room and uses the "Load Position" buttons on the handheld user interface unit to return the table to the position for patient unloading. Alternatively, the system could issue the command to return to the original loading position from the computer screen.

Following is a more detailed description of the operation of the patient positioning assembly described above.

The next stage is the initial patient set-up stage. During this stage, the treatment planning files are downloaded, prior to patient entry into the treatment room. During the download of treatment files, the treatment position of the table is downloaded into the controller. The treatment position of the table is one of: a) a default table position for the beam path set selected; and b) a treatment position for the patient, the last time the same plan was used. Before the patient walks into the treatment room, one of the loading position buttons on the handheld remote control unit is pressed, so as to position the table in a pre-defined comfortable position for the patient to get onto the table. The patient is then immobilized, for example using thermoplastic masks and or other immobilization devices.

The "TREAT" key on the handheld remote control unit is used to position the table to the nominal treatment position. For head treatments, or if this is a second or subsequent treatments for the patient with the same plan, the nominal treatment position is adequate for further automatic positioning, and the operator can proceed to the user control console for automatic positioning of the patient. Otherwise, the table is further manually adjusted, using the handheld remote control unit, so that the anatomical target region of interest is within the imaging field of view. The operator then proceeds to the user control console, for automatic positioning of the patient.

The next stage is the initial image acquisition stage. During this stage, the operator acquires images, using the ACQUIRE button on the patient alignment screen in the user interface screen 300 (shown in FIG. 10). If necessary, imaging parameters may need to be adjusted. Some examples of these parameters are: x-ray parameters; de-selection of fiducials that may have migrated or otherwise difficult to track; and adjustment of rigid body parameters.

In one exemplary form of the invention, the next stage is the one-time table alignment stage. The user selects the "AUTO COUCH" button on the patient alignment screen. This brings up a Couch Adjustment interface screen, which contains the initial corrections obtained from the TLS unit of the controller. The initial corrections from TLS are editable. The "MOVE" button moves the table by the amount of corrections indicated in the window. The option to disable rotation corrections are available. The "AUTO ALIGN" button perform the first correction, and proceeds to complete the automatic alignment.

The next stage is the automatic table alignment stage. The "AUTO ALIGN" button in the Couch Adjustment interface screen performs the automatic alignment. Auto Align starts by making the initial correction in the Couch Adjustment interface, and proceeds to take additional images and perform the correction from the image, until one of the following conditions are met: the desired number of images in the Auto Alignment phase are acquired, and/or the residual corrections fall below the limits specified in the Auto Alignment interface.

The next stage is the patient re-alignment stage. Patient re-alignment is entered whenever the system encounters a recoverable error (including operator pause), and the system is resumed from this state. Patient re-alignment is handled the same way as patient alignment. In other words, after the initial acquisition, further adjustments can be done automatically using the "AUTO ALIGN" button in the Couch Adjustment interface.

The final stage is the treatment delivery stage. Treatment delivery is initiated when the corrective motions for the table fall below pre-specified limits for translations and rotations. The corrective motions downloaded to the robot includes translations and the specified set of rotations. The robot moves to the nominal position for the node, correct by the specified translation and rotation, and then enable the x-ray beam generator. At the end of dose delivery for the node, the robot proceeds to the next node in this nominal position.

The controller includes software for error detection, reporting, and correction. In one embodiment, the error handling software includes "operator pause" functionality. This functionality allows the user to stop image acquisition, if one is in progress, and return to a target alignment or realignment mode. The user can also stop the table motion, if one is in progress, and return to the target alignment/realignment mode. The user can also stop subsequent image acquisitions and table motions, if the "auto alignment" mode is in progress.

In one embodiment, the error handling software also includes functionality for handling TLS (target locating system) errors. Appropriate TLS errors, such as soft algorithm errors, and/or E-stop for hardware errors, are reported. Upon acknowledgement of the error, the controller can return to the alignment or re-alignment state. The user can stop subsequent image acquisitions and table motions, if "auto alignment" is in progress. During the initial alignment, the "patient out of bounds" error is disabled, but the "TREAT" button is disabled until the patient is within bounds.

In one embodiment, the error handling software includes functionality for handling table interface errors. Table interface errors such as communication errors are handled as soft errors, which require user acknowledgment, but do not engage an E-stop. In one embodiment, the error handling software includes functionality for handling E-stops. In this embodiment, an E-stop stops computer controlled table motion, using a dual redundant mechanism. The controller software stops generating any further motion command signals. The table controller hardware is disabled from table movement when an E-stop is engaged. Even when the E-stop is engaged, the table is capable of moving using the handheld user interface unit. On resumption from pause or a recoverable E-stop, the E-stop is cleared by system reset from the operator console, which then goes into a patient re-alignment state. At this stage, the user can use auto-align to refine the patient position. The RESUME button on the patient re-alignment screen enables resumption of treatment delivery.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A patient positioning assembly comprising:
   a patient support device to support a patient thereon;
   a robotic arm assembly coupled to the patient support device, wherein the robotic arm assembly comprises:
   a base member;
   a plate member rotatably mounted on said base member, wherein the plate member is configured to rotate about a first axis to translate the patient support device in a first degree of freedom;
   an arm extending between a first end and a second end, wherein said first end is rotatably attached to said plate member, wherein the arm is configured to rotate about a second axis to translate the patient support device in a second degree of freedom, wherein the first and second degrees of freedom are used for translations along mutually orthogonal x-, y-, and z-coordinate axes, and wherein said second end is a wrist assembly rotatably connected to the patient support device to allow the patient support device to rotate about roll-, pitch-, and yaw-axes for third, fourth, and fifth degrees of freedom.

2. The patient positioning assembly of claim 1, wherein said base member is configured to be rotatably mounted on a plinth.

3. A patient positioning assembly according to claim 1 further comprising a controller operatively connected to said robotic arm assembly to control the movement of said robotic arm assembly.

4. A patient positioning assembly according to claim 3, wherein said patient positioning assembly further comprises a sensor system to detect the position of said patient support device relative to a treatment coordinate system, and wherein said controller is operatively connected with said sensor system to receive position data of said patient support device.

5. A patient positioning assembly according to claim 1, wherein said patient support device comprises a seat with a back.

6. A patient positioning assembly comprising:
   a patient support device to patient support a patient thereon;
   a robotic arm assembly coupled to the patient support device, wherein the robotic arm assembly comprises:
     a base member;
     a plate member rotatably mounted on said base member, wherein the plate member is configured to rotate about a first axis to translate the patient support device in a first degree of freedom;
     a first arm having a first end rotatably attached to said plate member, and a second end, wherein the first arm is configured to rotate about a second axis to translate the patient support device in a second degree of freedom;
     a second arm having a first end rotatably attached to the second end of said first arm, and a second end, wherein the second arm is configured to rotate about a third axis to translate the patient support device in a third degree of freedom, wherein the first, second, and third degrees of freedom are used for translations along mutually orthogonal x-, y-, and z-coordinate axes, and wherein said second end is a wrist assembly rotatably connected to the patient support device to allow the patient support device to rotate about roll-, pitch-, and yaw-axes for third, fourth, and fifth degrees of freedom.

7. A patient positioning assembly according to claim 6, wherein said base member is configured to be rotatably mounted on a plinth.

8. A patient positioning assembly according to claim 6 further comprising a controller operatively connected to said robotic arm assembly to control the movement of said robotic arm assembly.

9. A patient positioning assembly according to claim 8, wherein said patient positioning assembly further comprises a sensor system to detect the position of said patient support device relative to a treatment coordinate system, and wherein said controller is operatively connected with said sensor system to receive position data of said patient support device.

10. A patient positioning assembly according to claim 6, wherein said patient support device comprises a seat with a back.

* * * * *